(12) United States Patent
Bronkalla et al.

(10) Patent No.: US 10,176,569 B2
(45) Date of Patent: Jan. 8, 2019

(54) MULTIPLE ALGORITHM LESION SEGMENTATION

(71) Applicant: INTERNATIONAL BUSINESS MACHINES CORPORATION, Armonk, NY (US)

(72) Inventors: Mark Bronkalla, Hartland, WI (US); Sun Young Park, San Diego, CA (US); Dustin Sargent, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 14 days.

(21) Appl. No.: 15/258,832

(22) Filed: Sep. 7, 2016

(65) Prior Publication Data
US 2018/0068436 A1 Mar. 8, 2018

(51) Int. Cl.
*G06K 9/00* (2006.01)
*G06T 7/00* (2017.01)
*G06T 7/20* (2017.01)
*G06T 5/00* (2006.01)
*A61B 5/00* (2006.01)
*A61B 5/055* (2006.01)
(Continued)

(52) U.S. Cl.
CPC .......... *G06T 7/0012* (2013.01); *A61B 5/0022* (2013.01); *A61B 5/055* (2013.01); *A61B 5/7207* (2013.01); *A61B 6/032* (2013.01); *A61B 6/5264* (2013.01); *A61B 8/5276* (2013.01); *G06T 5/00* (2013.01); *G06T 7/0024* (2013.01); *G06T 7/0081* (2013.01); *G06T 7/20* (2013.01); *G06T 2207/20112* (2013.01)

(58) Field of Classification Search
None
See application file for complete search history.

(56) References Cited

U.S. PATENT DOCUMENTS 7,209,578 B2 4/2007 Saito et al.
8,090,429 B2 * 1/2012 Vija .................. A61B 6/00
382/282

(Continued)

FOREIGN PATENT DOCUMENTS

WO WO2015110932 A1 7/2015

OTHER PUBLICATIONS

Demner-Fushman et al., "Annotation and retrieval of clinically relevant images", Elsevier, 2009.

*Primary Examiner* — Matthew Bella
*Assistant Examiner* — Jose M Torres
(74) *Attorney, Agent, or Firm* — Erik Huestis; Stephen Kenny; Foley Hoag LLP

(57) ABSTRACT

Multiple algorithm lesion segmentation using an atlas is provided. In various embodiments, a plurality of medical images are read from an image repository. Each of the plurality of medical images has a source modality. Each of the plurality of medical images is registered to an anatomical atlas. An anatomical region depicted in each of the plurality of medical images is determined thereby. Based upon the source modality and the anatomical region depicted in each of the plurality of medical images, one of a plurality of segmentation algorithms is selected for each of the plurality of medical images. The selected segmentation algorithms are applied to each of the plurality of medical images. The results of the selected segmentation algorithms are displayed.

20 Claims, 4 Drawing Sheets

(51) Int. Cl.
  *A61B 6/00*   (2006.01)
  *A61B 8/08*   (2006.01)
  *A61B 6/03*   (2006.01)

(56) References Cited

U.S. PATENT DOCUMENTS

| | | |
|---|---|---|
| 8,320,651 B2 | 11/2012 | Vining et al. |
| 8,634,611 B2 | 1/2014 | Minakuchi et al. |
| 9,014,485 B2 | 4/2015 | Moehrle |
| 2002/0165837 A1* | 11/2002 | Zhang .................. B41J 2/16547 705/401 |
| 2003/0215120 A1* | 11/2003 | Uppaluri ................ A61B 6/482 382/128 |
| 2007/0014448 A1* | 1/2007 | Wheeler ............... G06T 7/0012 382/128 |
| 2009/0076853 A1 | 3/2009 | Sagawa |
| 2009/0226060 A1* | 9/2009 | Gering ...................... G06T 7/11 382/128 |
| 2010/0128954 A1* | 5/2010 | Ostrovsky-Berman ...................... G06T 7/11 382/131 |
| 2012/0177263 A1* | 7/2012 | Akinyemi ................. G06T 7/11 382/128 |
| 2014/0161338 A1* | 6/2014 | Machado ............. A61B 5/0042 382/131 |
| 2017/0124709 A1* | 5/2017 | Rithe ................... G06K 9/2036 |

* cited by examiner

MULTIPLE ALGORITHM LESION SEGMENTATION

BACKGROUND

Embodiments of the present invention relate to performing lesion segmentation analysis in medical images, and more specifically, to multiple algorithm lesion segmentation using an atlas.

BRIEF SUMMARY

According to embodiments of the present disclosure, methods of and computer program products for performing lesion segmentation analysis in medical images are provided. A plurality of medical images are read from an image repository. Each of the plurality of medical images has a source modality. Each of the plurality of medical images is registered to an anatomical atlas. An anatomical region depicted in each of the plurality of medical images is determined thereby. Based upon the source modality and the anatomical region depicted in each of the plurality of medical images, one of a plurality of segmentation algorithms is selected for each of the plurality of medical images. The selected segmentation algorithms are applied to each of the plurality of medical images. The results of the selected segmentation algorithms are displayed.

DETAILED DESCRIPTION

Figure 1:
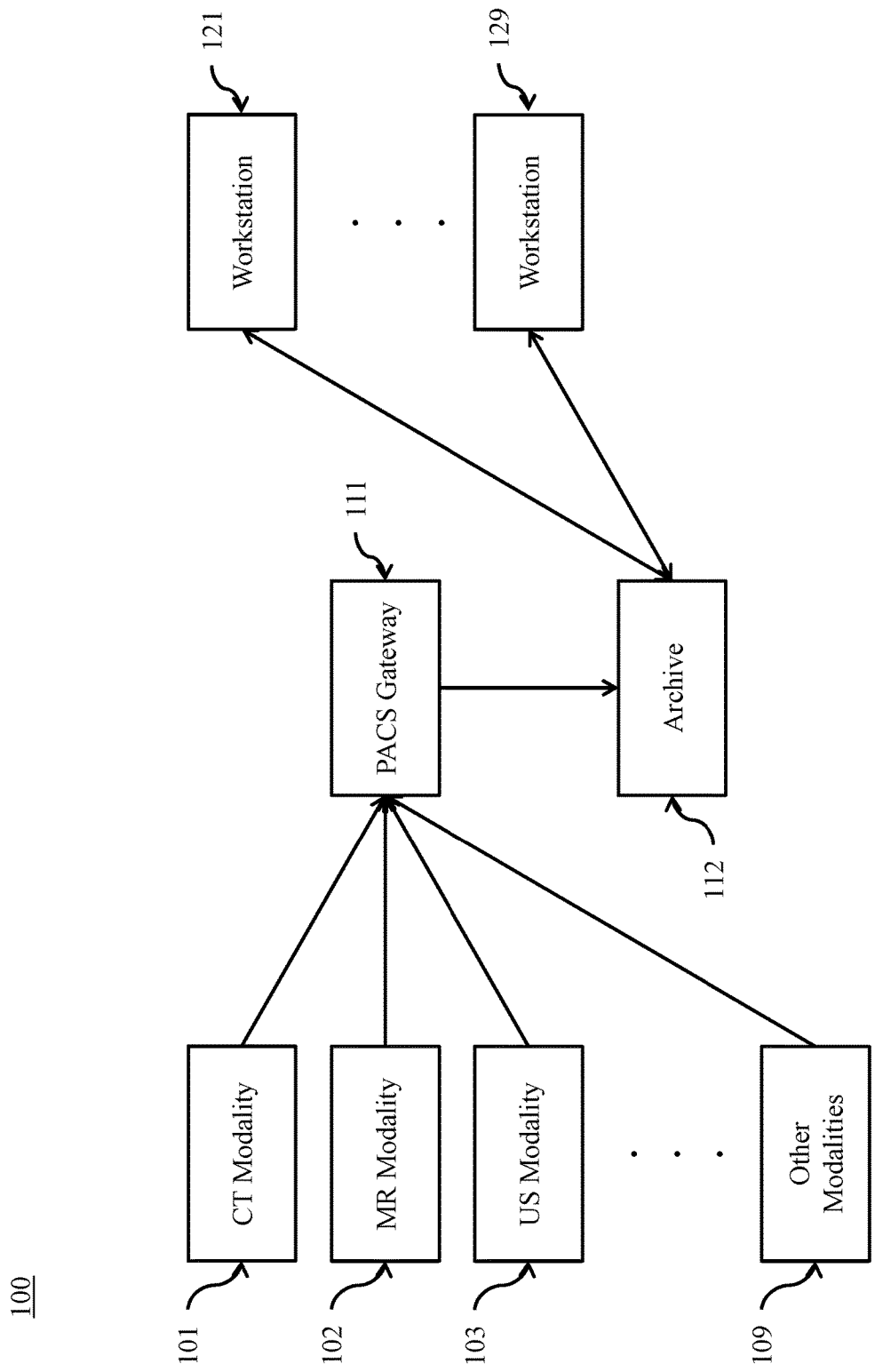
FIG. 1 depicts an exemplary Picture Archiving and Communication System.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

One of the more time consuming and tedious exercises in radiology is that of tracking the growth or shrinkage of tumors, cysts, or other structures over time. This is traditionally done by comparing multiple studies over a period of months or years. Studies may be of the same or different modalities (e.g., CT, MR, PET, NM). Standardized measurement techniques may be used such as RECIST, WHO, mass calculations, or longest dimension.

Existing solutions for automating this process are body part specific (e.g., prostate, liver, breast, lung), and modality specific (e.g., MR, CT, PET). Thus, a user must select an individual solution tailored to the anatomical region and modality at hand. This poses a significant challenge at high level cancer centers that are frequently referred patients with advanced disease states.

A cancer will often metastasize to additional regions of the body and different organs. An anatomically specific operation thus is extremely limiting, as multiple processes must be performed, often with differing user interfaces and interactions, and without a way to summarize the results from all of the affected anatomical regions. Algorithms needed for segmentation may vary by body part. In cases where the same algorithm is used, it may require differing tuning parameters for different organs or anatomical regions. In some embodiments, the segmentation algorithms are modular, for example in the form of plugins to the overall system. In some embodiments, such modular algorithms are downloadable.

Thus, there is a need for a system enabling the comprehensive comparison of studies. Accordingly, the present disclosure provides for annotating and tagging a lesion and assisting or automatically finding the corresponding lesion in subsequent studies. The present disclosure further provides for this facility across multiple anatomical areas and modalities. An anatomical atlas based approach and processes is provided for selecting among and applying multiple segmentation algorithms and aggregating the results. Although various examples provided herein focus on tumor or lesion segmentation, the present disclosure is applicable to other types of segmentation (e.g., neuro vascular).

According to various embodiments of the present disclosure, an anatomical atlas is used to identify all of the organs or regions imaged in a given exam. In some embodiments, this is performed as an automatic pre-processing step. In some embodiments, the step is performed by a cognitive computing platform. The anatomical atlas is registered to the imaging study and used to identify the organs or anatomical regions within that study. The atlas matching may be performed automatically in a manner hidden to the user.

According to various embodiments of the present disclosure, the registered anatomical atlas is used to automatically guide the selection of the most appropriate segmentation tools or algorithms for each organ or body part within the exam. These may then be applied automatically, as when carrying forward or backward previously identified lesions, or when a user manually selects a lesion for segmentation. In this way, the best algorithm and tuning are provided. Multiple segmentation algorithms and tuning parameters for each may be automatically applied for a variety of organs or anatomical regions, greatly reducing the workload for the user. In addition, accuracy is improved by reducing the chance of missing tumors or lesions, or of incorrect manual calculations of tumor size, volume or load.

According to various embodiments of the present disclosure, the aggregated results from the various segmentation algorithms are concisely presented to the user both visually on the image set and in tabular format. In some embodiments, the results are exported to a reporting package.

According to various embodiments of the present disclosure, the saved results also contain the linkage to the underlying algorithms or tunings used. Accordingly, on subsequent sessions when comparing to newer or older studies the same algorithms may preferentially be applied to ensure consistency in statistics on individual lesion or tumor shrinkage or growth. In cases where a system supports newer algorithms or tunings, these may be presented as an option to the user and then automatically run against not the current and prior studies to generate a new set of comparison statistics. Updates of prior statistics are particularly important where cognitive computing techniques are applied to segmentation, as the system is constantly learning and improving.

According to various embodiments of the present disclosure, the above-described atlas based approach is applied to CAD (Computer Aided Detection) and the automatic identification of lesions.

According to various embodiments of the present disclosure, the above-described atlas approach is used to automatically drive an over-read workflow. In such workflows, the study is ordered for a specific purpose but there is enough anatomical coverage to automatically look at other regions and highlight potential incidental findings. For example, a cardiac CT may be used for lung cancer screening.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
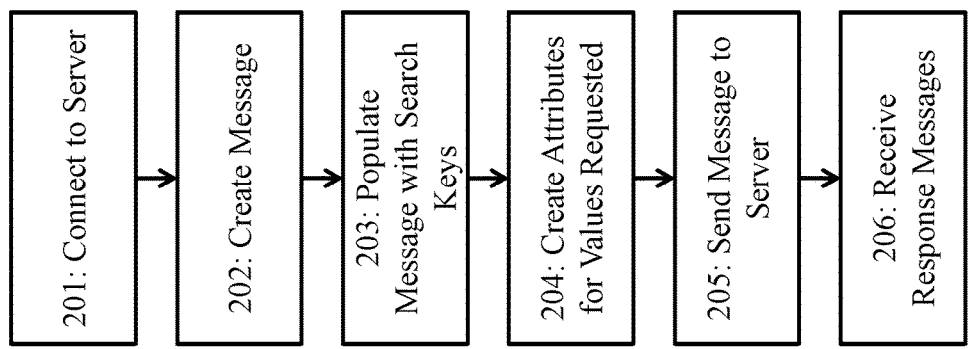
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 3:
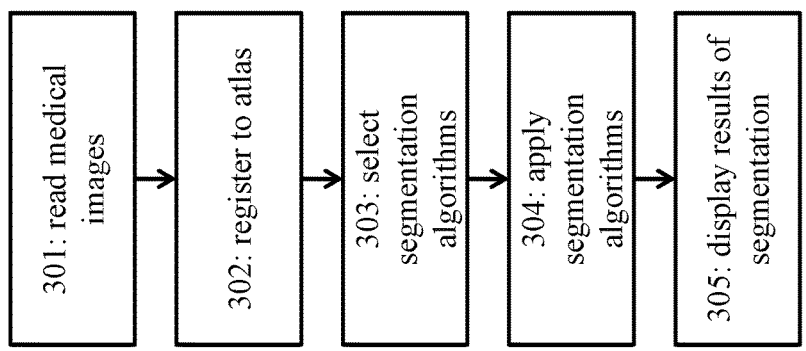
FIG. 3 illustrates a method for multiple algorithm lesion segmentation according to embodiments of the present disclosure.

Referring now to FIG. 3, a method 300 for lesion segmentation is illustrated according to embodiments of the present disclosure. At 301, a plurality of medical images are read from an image repository. Each of the plurality of medical images has a source modality. At 302, each of the plurality of medical images is registered to an anatomical atlas. An anatomical region depicted in each of the plurality of medical images is determined thereby. At 303, based upon the source modality and the anatomical region depicted in each of the plurality of medical images, one of a plurality of segmentation algorithms is selected for each of the plurality of medical images. At 304, the selected segmentation algorithms are applied to each of the plurality of medical images. At 305, the results of the selected segmentation algorithms are displayed. In some embodiments, displaying the results of the selected segmentation algorithms comprises displaying a time series of the plurality of medical images with the results of the selected segmentation algorithms displayed thereon. In some embodiments, the plurality of segmentation algorithms are modular. In some embodiments, the method further comprises preprocessing the image prior to applying the selected segmentation algorithms. In some embodiments, preprocessing the image comprises dynamic contrast enhancement, diffusion weighted imaging, or contrast subtraction. In some embodiments, preprocessing the image comprises registration to correct for motion artifacts. In some embodiments, the selected segmentation algorithm comprises 2D segmentation. In some embodiments, 2D segmentation comprises thresholding and morphological filtering. In some embodiments, 2D segmentation comprises applying a level set algorithm. In some embodiments, 2D segmentation comprises single or dual snakes. In some embodiments, 2D segmentation comprises application of a support vector machine. In some embodiments, the selected segmentation algorithm comprises building a 3D volume from 2D segmentation by propagation. In some embodiments, the propagation is tunable by propagation and termination parameters. In some embodiments, the parameters comprise threshold, texture, cost function, or propagation energy analysis parameters. In some embodiments, the selected segmentation algorithm comprises volumetric segmentation. In some embodiments, volumetric segmentation comprises fuzzy connectedness, watershed, or surface extraction by dynamic programming. In some embodiments, selecting one of a plurality of segmentation algorithms is based on an anatomy of interest, a modality, or an acquisition parameters. In some embodiments, applying the selected segmentation algorithms comprises applying tuning parameters based on the anatomical region depicted in each of the plurality of medical images, an acquisition modality, or an acquisition protocol.

Figure 4:
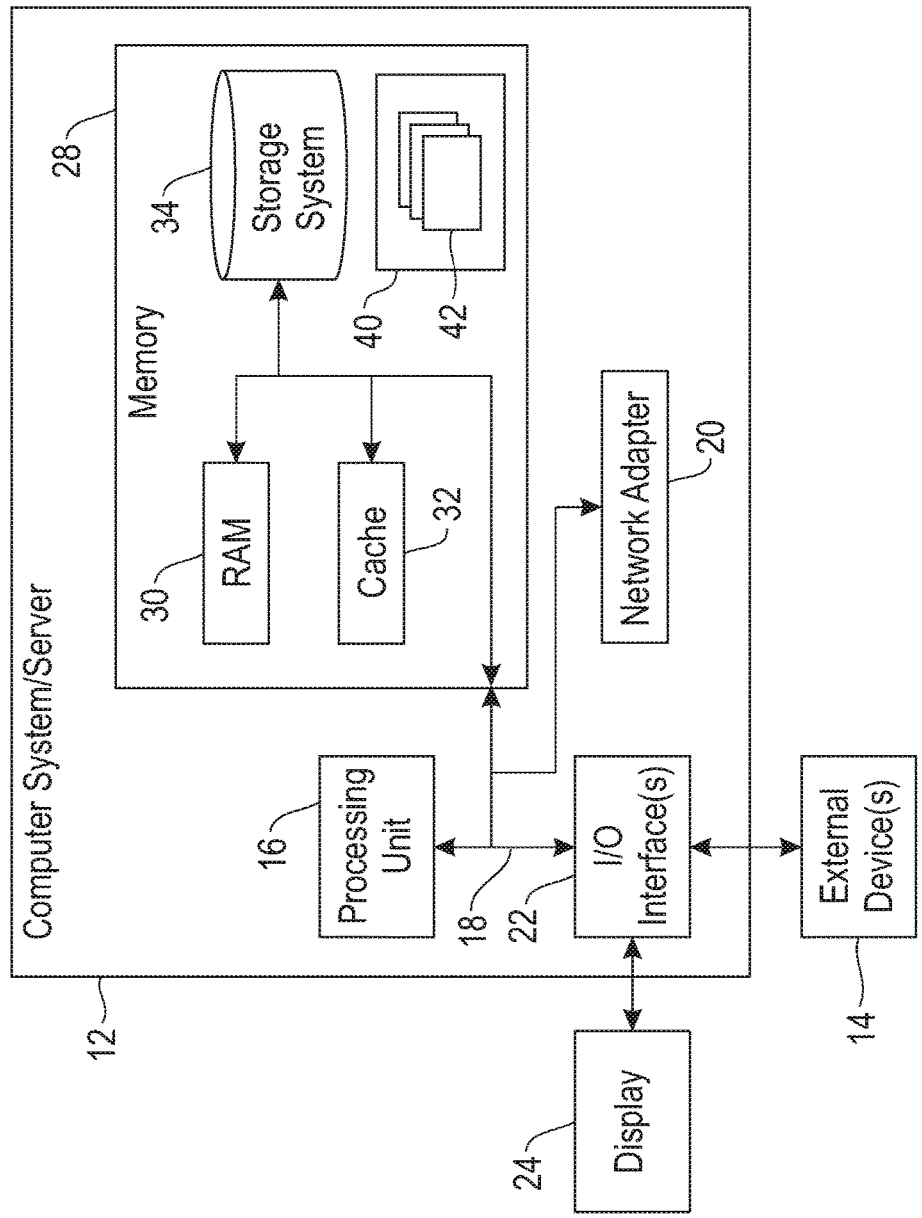
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a plurality of medical images from an image repository, a first of the plurality of medical images corresponding to a first body part and having a first source modality, and a second of the plurality of medical images corresponding to a second body part and having a second source modality different from the first source modality, the plurality of medical images being from sequential studies;
   registering each of the plurality of medical images to an anatomical atlas, thereby determining an anatomical region depicted in each of the plurality of medical images;
   based upon the first source modality and the anatomical region depicted in the first of the plurality of medical images, selecting a first segmentation algorithm for the first of the plurality of medical images;
   based upon the second source modality and the anatomical region depicted in the second of the plurality of medical images, selecting a second segmentation algorithm for the second of the plurality of medical images, the second segmentation algorithm different from the first segmentation algorithm;
   applying the first segmentation algorithm to the first of the plurality of medical images and the second segmentation algorithm to the second of the plurality of medical images, to annotate a lesion within the first and second of the plurality of medical images;
   displaying the results of the first and second segmentation algorithms, thereby providing aggregate results of the sequential studies.

2. The method of claim 1, wherein displaying the results of the first and second segmentation algorithms comprises displaying a time series of the plurality of medical images with the results of the first and second segmentation algorithms displayed thereon.

3. The method of claim 1, wherein the first and second segmentation algorithms are modular.

4. The method of claim 1, further comprising preprocessing the image prior to applying the first segmentation algorithm.

5. The method of claim 4, wherein preprocessing the image comprises dynamic contrast enhancement, diffusion weighted imaging, or contrast subtraction.

6. The method of claim 4, wherein preprocessing the image comprises registration to correct for motion artifacts.

7. The method of claim 1, wherein the first and second segmentation algorithms each comprises 2D segmentation.

8. The method of claim 7, wherein 2D segmentation comprises thresholding and morphological filtering.

9. The method of claim 7, wherein 2D segmentation comprises applying a level set algorithm.

10. The method of claim 7, wherein 2D segmentation comprises single or dual snakes.

11. The method of claim 7, wherein 2D segmentation comprises application of a support vector machine.

12. The method of claim 1, wherein the first and second segmentation algorithms each comprises building a 3D volume from 2D segmentation by propagation.

13. The method of claim 12, wherein the propagation is tunable by propagation and termination parameters.

14. The method of claim 13, wherein the parameters comprise threshold, texture, cost function, or propagation energy analysis parameters.

15. The method of claim 1, wherein the first and second segmentation algorithms each comprises volumetric segmentation.

16. The method of claim 15, wherein volumetric segmentation comprises fuzzy connectedness, watershed, or surface extraction by dynamic programming.

17. The method of claim 1, wherein selecting the first segmentation algorithm and selecting the second segmentation algorithm are based on an anatomy of interest, a modality, or an acquisition parameter.

18. The method of claim 1, wherein applying the first segmentation algorithm comprises applying tuning parameters based on the anatomical region depicted in the first of the plurality of medical images, an acquisition modality, or an acquisition protocol; and
wherein applying the second segmentation algorithm comprises applying tuning parameters based on the anatomical region depicted in the second of the plurality of medical images, an acquisition modality, or an acquisition protocol.

19. A computer program product for lesion segmentation, the computer program product comprising a computer readable storage medium having program instructions embodied therewith, the program instructions executable by a processor to cause the processor to perform a method comprising:
reading a plurality of medical images from an image repository, a first of the plurality of medical images corresponding to a first body part and having a first source modality, and a second of the plurality of medical images corresponding to a second body part and having a second source modality different from the first source modality, the plurality of medical images being from sequential studies;
registering each of the plurality of medical images to an anatomical atlas, thereby determining an anatomical region depicted in each of the plurality of medical images;
based upon the first source modality and the anatomical region depicted in the first of the plurality of medical images, selecting a first segmentation algorithm for the first of the plurality of medical images;
based upon the second source modality and the anatomical region depicted in the second of the plurality of medical images, selecting a second segmentation algorithm for the second of the plurality of medical images, the second segmentation algorithm different from the first segmentation algorithm;
applying the first segmentation algorithm to the first of the plurality of medical images and the second segmentation algorithm to the second of the plurality of medical images, to annotate a lesion within the first and second of the plurality of medical images;
displaying the results of the first and second segmentation algorithms, thereby providing aggregate results of the sequential studies.

20. A system comprising:
an image repository;
an anatomical atlas;
a computing node having program instructions embodied therewith, the program instructions executable by a processor of the computing node to cause the processor to perform a method comprising:
reading a plurality of medical images from the image repository, of the plurality of medical images corresponding to a first body part and having a first source modality, and a second of the plurality of medical images corresponding to a second body part and having a second source modality different from the first source modality, the plurality of medical images being from sequential studies;
registering each of the plurality of medical images to the anatomical atlas, thereby determining an anatomical region depicted in each of the plurality of medical images;
based upon the first source modality and the anatomical region depicted in the first of the plurality of medical images, selecting a first segmentation algorithm for the first of the plurality of medical images;
based upon the second source modality and the anatomical region depicted in the second of the plurality of medical images, selecting a second segmentation algorithm for the second of the plurality of medical images, the second segmentation algorithm different from the first segmentation algorithm;
applying the first segmentation algorithm to the first of the plurality of medical images and the second segmentation algorithm to the second of the plurality of medical images, to annotate a lesion within the first and second of the plurality of images;
displaying the results of the first and second segmentation algorithms on a display of the computing node, thereby providing aggregate results of the sequential studies.

* * * * *